United States Patent [19]
Lange et al.

[11] Patent Number: 5,973,195
[45] Date of Patent: Oct. 26, 1999

[54] SURFACTANTS DERIVED FROM 2-(2-HYDROXYPHENYL)BENZENESULFINATE AND ALKYL-SUBSTITUTED DERIVATIVES

[75] Inventors: Elaine A. Lange, Bellaire; Qun Lin, Spring, both of Tex.; Kurt R. Nielsen, Chadds Ford, Pa.; Christopher C. Dooyema, Houston, Tex.

[73] Assignee: Energy BioSystems Corporation, The Woodlands, Tex.

[21] Appl. No.: 09/044,272

[22] Filed: Mar. 19, 1998

[51] Int. Cl.$^6$ ........................................ C07F 5/02
[52] U.S. Cl. .................. 562/59; 562/46; 562/45
[58] Field of Search .................. 562/46, 45, 59

[56] References Cited

U.S. PATENT DOCUMENTS

| | | | |
|---|---|---|---|
| 2,271,635 | 2/1942 | Flett .......................................... | 510/290 |
| 4,338,258 | 7/1982 | Brinkwertth et al. .................. | 558/413 |
| 5,104,801 | 4/1992 | Kilbane, II .............................. | 435/282 |
| 5,132,219 | 7/1992 | Kilbane, II .............................. | 435/195 |
| 5,232,854 | 8/1993 | Monticello .............................. | 435/282 |
| 5,344,778 | 9/1994 | Kilbane, II .............................. | 435/262 |
| 5,356,801 | 10/1994 | Rambosek et al. ..................... | 435/195 |
| 5,356,813 | 10/1994 | Monticello .............................. | 435/282 |
| 5,358,869 | 10/1994 | Kilbane, II .............................. | 435/282 |
| 5,358,870 | 10/1994 | Monticello et al. ..................... | 435/282 |
| 5,387,523 | 2/1995 | Monticello .............................. | 435/282 |
| 5,472,875 | 12/1995 | Monticello .............................. | 435/282 |
| 5,607,857 | 3/1997 | Grossman et al. ...................... | 435/282 |

OTHER PUBLICATIONS

Omori, T., et al., "Desulfurization of Dibenzothiophene by Corynebacterium sp. Strain SY1," *Appl. Env. Microbiol.*, 58(3): 911–915 (1992).

Izumi, Y., et al., "Selective Desulfurization of Dibenzothiophene by *Rhodococcus erythropolis* D–1," *Appl. Env. Microbiol.*, 60(1): 223–226 (1994).

Lee, M.K., et al., "Sulfur–Specific Microbial Desulfurization of Sterically Hindered Analogs of Dibenzothiophene," *Appl. Environ. Microbiol.*, 61(12): 4362–4366 (1995).

*Primary Examiner*—Gary Geist
*Assistant Examiner*—Taylor V. Oh
*Attorney, Agent, or Firm*—Hamilton, Brook, Smith & Reynolds, P.C.

[57] ABSTRACT

The present invention relates to compounds having utility as surfactants which are derived from intermediates produced in petroleum biodesulfurization processes. The compounds of the invention include acyloxybiphenylsulfinates, acyloxybiphenylsulfonates, alkyl sulfinatobiphenyl ethers and alkyl sulfonatobiphenyl ethers. The invention also provides methods of producing these compounds.

11 Claims, No Drawings

SURFACTANTS DERIVED FROM 2-(2-HYDROXYPHENYL)BENZENESULFINATE AND ALKYL-SUBSTITUTED DERIVATIVES

BACKGROUND OF THE INVENTION

Surfactants are amphiphilic compounds comprising a polar or ionic head group and a hydrophobic tail. Anionic surfactants have important commercial applications as wetting agents and detergents. For example, current methods for removing petroleum from underground reserves typically leave a substantial amount of unrecoverable residual oil. One approach to the recovery of this residual petroleum is surfactant-based enhanced oil recovery. In this method, an aqueous surfactant solution is injected into an oil well at a late stage of depletion to extract the residual oil. Development of such enhanced oil recovery methods was an area of active research in the petroleum industry in the 1970s and 1980s and resulted in several pilot field processes.

Surfactants typically used in enhanced oil recovery processes have sulfonate or sulfate polar head groups due to the aqueous solubility of such compounds in the presence of hard cations often present in such environments, such as $Mg^{2+}$ and $Ca^{2+}$. Such surfactants include alkylsulfonates, alkylarylsulfonates and petroleum sulfonates. More recently, the development of surfactant-based enhanced oil recovery methods has declined dramatically, due, in part, to high surfactant costs. As a result, the development of low-cost surfactants derived from waste products, such as lignin, is an active area of research in the petroleum industry.

There is, thus, a need for a surfactant suitable for use in an enhanced oil recovery process which is derived from inexpensive starting materials.

SUMMARY OF THE INVENTION

The present invention relates to compounds having utility as surfactants which are derived from intermediates produced in petroleum biodesulfurization processes. The compounds of the invention include substituted biphenylsulfinates, biphenylsulfonates and biphenyl disulfonates. The substituents can occur on either or both rings of the biphenyl unit and can include straight chain, branched or cyclic, substituted or unsubstituted $C_1$–$C_{24}$-alkyl groups. The compounds also include at least one additional substituent, such as an alkylcarboxy, alkylsufonoxy, alkoxy, alkylcarbonyl, oligo(ethylene oxide) or oligo(propylene oxide) group.

The invention also provides methods of producing the compounds of the invention. For example, the method of producing an acyloxybiphenylsulfinate compound comprises the step of contacting a hydroxybiphenylsulfinate compound with a carboxylic acid or an activated carboxylic acid under conditions sufficient for acylation of the hydroxybiphenylsulfinate compound, thereby producing an acyloxybiphenylsulfinate compound. A similar method starting with an acyloxybiphenylsulfonate compound can be used to produce an acyloxybiphenylsulfonate compound.

The invention also provides a method for preparing an alkyl sulfinatobiphenyl ether compound. The method comprises the step of reacting an hydroxybiphenylsulfinate compound with an alkylating agent under conditions suitable for alkylation of the hydroxybiphenylsulfinate compound, thereby producing an alkyl sulfinatobiphenyl ether compound. A similar method starting with an hydroxybiphenylsulfonate compound can be used to produce an alkyl sulfonatobiphenyl ether.

The present invention provides useful surfactant compounds and methods of preparation thereof using starting materials which are available as intermediates in the biocatalytic desulfurization of fossil fuels. The invention, thus, provides a method for converting these intermediates into useful compounds, thereby eliminating or reducing the need for their further processing or disposal.

DETAILED DESCRIPTION OF THE INVENTION

The present invention provides novel compounds which are useful as surfactants, as starting materials for the production of surfactants or as wetting agents.

The term "acyloxybiphenylsulfinate compound" refers to an ester of, for example, a carboxylic acid with a hydroxybiphenylulfinate compound or a susbtituted derivative thereof. The term "acyloxybiphenylsulfonate compound" refers to a compound which is an ester of, for example, a carboxylic acid with a hydroxybiphenylsulfonate compound or a substituted derivative thereof.

The term "alkyl sulfinatobiphenyl ether" refers to a compound which is an ether resulting from alkylation of the hydroxyl oxygen atom of a hydroxybiphenylsulfinate compound. The term "alkyl sulfonatobiphenyl ether" refers to an ether which results from alkylation of the hydroxyl oxygen atom of a hydroxybiphenylsulfonate compound.

The suffix "-sulfinate" and the prefix "sulfinato-" as used herein indicate a compound comprising a sulfinate (—S(O)O⁻, deprotonated) or sulfinic acid (—S(O)OH, protonated) functional group. The protonation state of a sulfinate group is dependent on pH. Chemical names used herein which include the suffix "sulfinate" or the prefix "sulfinato" can refer to either protonation state of the compound. In the deprotonated state, a sulfinate compound will be associated with an appropriate counter cation, such as a sodium, potassium, calcium or ammonium ion.

The suffix "-sulfonate" and the prefix "sulfonato-" as used herein indicates a compound comprising a sulfonate (—S(O)₂O⁻, deprotonated) or sulfonic acid (—S(O)₂OH, protonated) functional group. The protonation state of a sulfonate group is dependent on pH. Chemical names used herein which include the suffix "-sulfonate" or the prefix "sulfonato" refer to either protonation state of the compound. In the deprotonated state, a sulfinate compound will be associated with an appropriate counter cation, such as a sodium, potassium, calcium or ammonium ion.

Preferred compounds of the invention include compounds of Formula I,

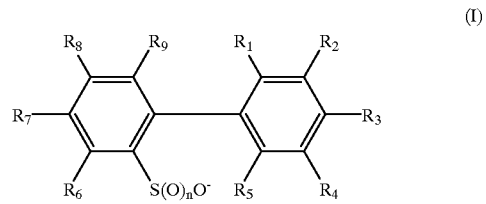

(I)

wherein n is 1 or 2 and $R_2$–$R_9$ are each, independently, hydrogen or a substituent such as a normal, branched or cyclic, substituted or unsubstituted alkyl group, a substituted or unsubstituted aryl group, an amino group, a hydroxyl group, a cyano group, an acyl group, a nitro group, or a halogen atom, such as a fluorine, chlorine, bromine, or iodine atom. Preferably, $R_2$–$R_9$ are each, independently, a hydrogen atom, a substituted or unsubstituted linear, branched or cyclic $C_1$–$C_{24}$-alkyl group, or another group which can be substituted on a dibenzothiophene compound obtained from a fossil fuel, such as petroleum. Suitable alkyl substituents include halogen atoms, aryl groups, alkoxy groups, nitrile groups, acyl groups, amino groups and hydroxyl groups. In one embodiment, $R_1$ is a YC(O)O—, YO— or YS(O)$_2$O— group, wherein Y is a hydrophobic group, such as a saturated or unsaturated, normal, branched or cyclic, substituted or unsubstituted $C_3$–$C_{24}$-hydrocarbyl group. Y is, preferably, a normal, branched or cyclic, substituted or unsubstituted $C_6$–$C_{24}$-alkyl group. Suitable alkyl substituents include halogen atoms, such as fluorine, chlorine, bromine and iodine atoms; and aryl groups, such as phenyl and naphthyl groups.

In another embodiment, the present invention provides compounds of Formula I wherein $R_1$ is an oligo(ethylene oxide) moiety of the formula HOCH$_2$CH$_2$(OCH$_2$CH$_2$)$_m$O— or an oligo(propylene oxide) moiety of the formula CH$_3$CH(OH)CH$_2$(OCH(CH$_3$)CH$_2$)$_m$O—, where m is an integer from 0 to about 20. Compounds of this type are useful as wetting agents.

The present invention also provides biphenyl disulfonate compounds of Formula II,

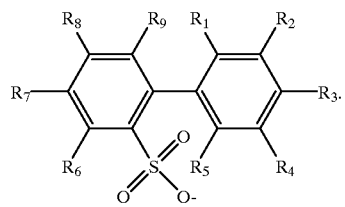

(II)

In this formula, $R_6$–$R_9$ are each, independently, a hydrogen atom or a straight chain or branched $C_1$–$C_{24}$-alkyl group. At least one of $R_2$–$R_5$ is a sulfonate group and the remainder are each, independently, a hydrogen atom or a straight chain or branched $C_1$–$C_{24}$-alkyl group. $R_1$ is as defined for Formula I, above, and can additionally be a hydroxyl group.

The present invention also provides a method of producing an acyloxybiphenylsulfinate compound. The method comprises the step of contacting a hydroxybiphenylsulfinate compound, or a substituted derivative thereof, with a carboxylic acid or an activated carboxylic acid under conditions sufficient for acylation of the hydroxy group, thereby producing an acyloxybiphenylsulfinate compound.

An "activated carboxylic acid", as the term is used herein, is a carboxylic acid derivative in which the —C(=O)OH moiety is replaced by a —C(=O)—X moiety, wherein X is a leaving group. A variety of suitable leaving groups are well known in the art; examples include halide ions, such as chloride, bromide and iodide atoms; the p-toluenesulfonate group, the methanesulfonate group, the 1-imidazolyl group and carboxylate groups. The activated carboxylic acid is preferably an acyl chloride, an acyl p-toluenesulfonate, or an acid anhydride.

In a preferred embodiment the carboxylic acid or activated carboxylic acid is of the formula Y—C(=O)X, wherein Y is a hydrophobic group, such as a normal or branched, substituted or unsubstituted $C_3$–$C_{24}$-alkyl group, and X is —OH or a suitable leaving group, as described above. Suitable alkyl substituents include halogen atoms, such as fluorine, chlorine, bromine and iodine atoms; and aryl groups, such as phenyl and naphthyl groups. In a particularly preferred embodiment, $R_1$ is a normal or branched $C_6$–$C_{24}$-alkyl group.

The hydroxybiphenylsulfinate compound is preferably a substituted or unsubstituted 2-(2-hydroxyphenyl) benzenesulfinate compound of Formula III,

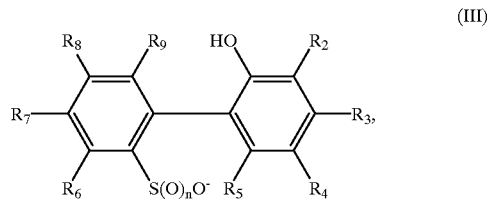

(III)

wherein $R_2$–$R_9$ are each, independently, hydrogen, a normal or branched, substituted or unsubstituted alkyl group, a substituted or unsubstituted aryl group, an hydroxyl group, a cyano group, a nitro group or a halogen atom, such as a fluorine, chlorine, bromine or iodine atom, and n is 1. Suitable alkyl substitutents include halogen atoms, such as fluorine, chlorine, bromine and iodine atoms; aryl groups, such as phenyl and naphthyl groups, alkoxy groups, acyl groups, amino groups and hydroxyl groups. Preferably, $R_2$–$R_9$ are each, independently, a hydrogen atom or a linear, branched or cyclic $C_1$–$C_6$-alkyl group.

In another embodiment, the invention provides a method of forming an acyloxybiphenylsulfonate compound. The method comprises contacting a hydroxybiphenylsulfonate compound with a carboxylic acid or activated carboxylic acid under conditions sufficient for acylation of the hydroxy group, thereby producing an acyloxybiphenylsulfonate compound. In a preferred embodiment, the hydroxybenzenesulfonate compound is of Formula III,

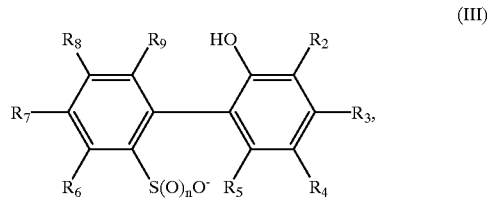

(III)

wherein $R_2$–$R_9$ are each, independently, hydrogen, a normal or branched, substituted or unsubstituted alkyl group, a substituted or unsubstituted aryl group, an hydroxyl group, a cyano group, a nitro group or a halogen atom, such as a fluorine, chlorine, bromine or iodine atom and n is 2. Suitable alkyl substitutents include halogen atoms, such as fluorine, chlorine, bromine and iodine atoms; and aryl groups, such as phenyl and naphthyl groups. Preferably, each R is, independently, a hydrogen atom or a linear or branched $C_1$–$C_6$-alkyl group. The carboxylic acid or activated carboxylic acid is preferably of the formula YC(=O)X, wherein X and Y have the meanings stated above.

Reaction conditions suitable for acylation of the hydroxyl oxygen atom are well known in the art and can be determined without undue experimentation. For example, the reaction will typically take place in solution, such as in an aqueous solvent, an organic solvent or a mixed aqueous/ organic solvent. The choice of solvent depends, in part, on the solubilities of the reactants and the nature of the acylating agent. For example the hydroxybiphenylsulfinate or hydroxybiphenylsulfonate compound can be acylated with a carboxylic acid in the presence of a concentrated strong acid, such as sulfuric acid or hydrochloric acid. Acylation of the hydroxybiphenylsulfinate or hydroxybiphenylsulfonate compound, for example, with an acyl chloride or acid anhydride can be performed in an organic solvent, preferably in the presence of a base, such as pyridine. Sulfonoxybiphenylsulfinate and sulfonoxybiphenylsulfonate compounds, for example, compounds of Formula I in which $R_1$ is $YS(O)_2O—$, can be prepared by reacting a hydroxybiphenylsulfinate compound or a hydroxybiphenylsulfonate compound, respectively, with a sulfonic acid $YSO_3H$ or an activated sulfonic acid $YSO_3X$, where X is a suitable leaving group, such as a halide ion, for example, chloride. Suitable conditions for sulfonylation of an phenolic hydroxyl group are known in the art.

Alkyl sulfinatobiphenyl ether compounds can be prepared by a method comprising the step of reacting a hydroxybiphenylsulfinate compound with an alkylating agent under conditions suitable for the alkylation of the hydroxyl oxygen atom of the hydroxybiphenylsulfinate compound. An alkyl sulfonatobiphenyl ether compound can be produced by a similar method comprising reacting a hydroxybiphenylsulfonate compound with a suitable alkylating agent under conditions suitable for alkylation of the hydroxyl oxygen atom. Preferably, the alkylating agent is of the general formula Y-X, where Y is a normal, branched or cyclic alkyl or substituted alkyl group and x is a suitable leaving group, such as a halide, for example, chloride, bromide or iodide, p-toluenesulfonate, methanesulfonate and others which are known in the art. In one embodiment, the alkylating agent is an alkyl halide and the alkylation is carried out under basic conditions. Preferably, Y is a normal or branched $C_6-C_{24}$-alkyl group.

The hydroxybiphenylsulfonate compound can, optionally, be prepared by contacting a hydroxybiphenylsulfinate compound with an oxidant as discussed above under sufficient conditions for oxidation of the sulfinate group to a sulfonate group, thereby forming a hydroxybiphenylsulfonate compound. In a preferred embodiment, the hydroxybiphenylsulfinate starting compound is of Formula II, as described above. Similarly, acyloxybiphenylsulfinate compounds and sulfonoxybiphenylsulfinate compounds can be oxidized to form acyloxybiphenylsulfonate compounds and sulfonoxybiphenylsulfinate compounds, respectively, while an alkyl sulfinatobiphenyl ether can be oxidized to produce an alkyl sulfonatobiphenyl ether. For example, a compound of Formula I wherein n=1 can be oxidized to form the corresponding compound with n=2.

The sulfinate group can be oxidized to a sulfonate group by reacting the sulfinate compound with a suitable oxidant, as is known in the art. Examples of suitable oxidants for this transformation include nitric acid, dioxygen, peroxides, such as hydrogen peroxide, m-chloroperbenzoic acid, peracetic acid and other peracids, hypochlorite, dimethyl sulfoxide, chromic acid, permanganate, dioxiranes, perborate and other oxidants which are well known in the art.

Compounds of Formula I in which $R_1$ is an oligo(ethylene oxide) or oligo(propylene oxide) group can be prepared by contacting a compound of Formula III with ethylene oxide or propylene oxide under suitable conditions. For example, an alkaline aqueous solution of a compound of Formula III can be contacted with ethylene oxide or propylene oxide under an inert atmosphere, for example, a dinitrogen atmosphere, at elevated temperature, to produce a compound of Formula I wherein $R_1$ is an oligo(ethylene oxide) or oligo(propylene oxide) moiety. A sulfinate compound of Formula I in which $R_1$ is an oligo(ethylene oxide) or oligo(propylene oxide) group can be oxidized to produce the corresponding sulfonate compound by contacting the sulfinate compound with a suitable oxidant, as described above.

A compound of Formula II can be prepared by sulfonating a compound of Formula III or Formula I in which at least one of $R_2$ to $R_5$ is a hydrogen atom. Suitable sulfonation conditions are known in the art. In one embodiment, the compound of Formula I or Formula III is contacted with dilute or concentrated sulfuric acid or fuming sulfuric acid under conditions suitable for sulfonation.

2-(2-Hydroxyphenyl)benzenesulfinate occurs as an intermediate in the biocatalytic desulfurization of a fossil fuel containing dibenzothiophene. Thus, the starting material for the formation of the compounds of the invention is advantageously derived from a petroleum biodesulfurization process. Suitable biodesulfurization processes and catalysts for use therein are described in U.S. Pat. Nos. 5,104,801; 5,358,869; 5,132,219; 5,344,778; 5,472,875; 5,232,854; 5,387,523; 5,356,813; 5,356,801 and 5,358,870, as well as U.S. patent application Ser. Nos. 08/351,754; 08/735,963; 08/933,885; 08/851,088; 08/851,089 and 08/715,554. For example, suitable biocatalysts for the oxidation of dibenzothiophene to 2-(2-hydroxyphenyl)benzenesulfinate include Rhodococcus sp. IGTS8, Corynebacterium sp. strain SY1, as disclosed by Omori et al., *Appl. Env. Microbiol.*, 58: 911–915 (1992); *Rhodococcus erythropolis* D-1, as disclosed by Izumi et al., *Appl. Env. Microbiol.*, 60:223–226 (1994); the Arthrobacter strain described by Lee et al., *Appl. Environ. Microbiol.* 61: 4362–4366 (1995) and the Rhodococcus strains (ATCC 55309 and ATCC 55310) disclosed by Grossman et al., U.S. Pat. No. 5,607,857, and Sphingomonas sp. strain AD109, as described in U.S. patent application Ser. No. 08/851,089, each of which is incorporated herein by reference in its entirety. Other suitable biocatalysts include recombinant organisms containing heterologous desulfurization genes, as disclosed, for example, in U.S. patent application Ser. No. 08/851,088, incorporated herein by reference.

EXAMPLES

Example 1

Reaction of 2-(2-hydroxyphenyl)benzenesulfonate with n-decanoic acid

An aqueous solution of HPBS at neutral pH was treated with 1.5 equivalents $H_2O_2$. The reaction mixture was maintained at room temperature for 9 hr. A platinum on carbon catalyst was then added to destroy residual peroxide and the catalyst was removed by filtration. The filtrate was freeze dried to afford a solid, which was identified as 2-(2-hydroxyphenyl)benzenesulfonate ($HPBSO_3$) by liquid chromatography/mass spectrometry.

Reaction of $HPBSO_3$ with Decanoic Acid $HPBSO_3$ (0.1 g), excess decanoic acid and a catalytic amount of sulfuric acid were added to toluene and the resulting mixture was heated to reflux for 30 min. The reaction mixture was then cooled, diluted with water and neutralized with $NaHCO_3$. The formation of a product was confirmed qualitatively by liquid chromatography. Analysis of the reaction mixture by LC-MS showed unreacted starting materials and a small amount of a third compound with MW=403 9/mol, the molecular weight of the expected ester product.

Example 2

Reaction of $HPBSO_3$ with Dodecanoic Anhydride $HPBSO_3$ was mixed with 2 mole equivalents of dodecanoic anhydride and a catalytic amount of pyridine. The mixture was heated to 120° C. for 15 min, then cooled and extracted with diethyl ether. The ether extract was washed with water. The water extract was analyzed by LC-MS and found to contain a product of molecular weight 432.5, as expected for the dodecanoate ester of $HPBSO_3$.

Example 3

Reaction of $HPBSO_3$ with Octyl Bromide $HPBSO_3$ was reacted with octyl bromide following the general method disclosed in Carr et al., *J. Am. Chem. Soc.* 69: 1170–1172 (1943). $HPBSO_3$ was dissolved in a 1:1 mixture of 15% aqueous NaOH and methanol. octyl bromide was added, and the mixture was heated to reflux for 15 hr. Analysis of the resulting solution by LC/MS indicated the presence of a product of molecular weight 362, as expected for the octyl ether of $HPBSO_3$.

Example 4

Synthesis of 2-(2-hydroxy-sulfonato)phenyl Benzenesulfonate

A sample of HPBSO3 was dissolved in 80% sulfuric acid and the resulting solution was maintained for 2.5 hours at 60° C. The solution was then analyzed by liquid chromatography/mass spectrometry and a fraction having a molecular weight of 329 was observed, as expected for the singly charged anion of 2-(2-hydroxy-sulfonatophenyl) benzenesulfinate.

A similar reaction was performed starting with n-decyl 2-(2-sulfonatophenyl)phenyl ether. A fraction of molecular weight, 234 was observed, corresponding to the doubly charged anion of 2-(2-n-decyloxy-sulfonatophenyl) benzenesulfonate.

Example 5

Reaction of $HPBSO_3$ with Propylene Oxide

An aqueous solution of $HPBSO_3$ and 40 equivalents of propylene oxide were sealed in a pressure reaction tube and heated to 50° C. for 2 days. Liquid chromatography/mass spectromety analysis of the resulting solution revealed the presence of compounds of molecular weight 307, 365 and 423, corresponding to the addition of 1, 2 and 3 propylene oxide groups, respectively.

EQUIVALENTS

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

We claim:
1. A compound of Formula I,

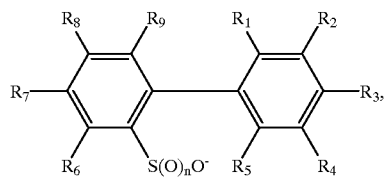

(I)

wherein $R_2$–$R_9$ are each, independently, hydrogen, a substituted or unsubstituted, normal, branched or cyclic alkyl group, a substituted or unsubstituted aryl group, an hydroxyl group, a cyano group, a nitro group or a halogen atom; $R_1$ is a moiety of the formula YC(O)O— or YO—, wherein Y is a hydrophobic group; and n is 1 or 2.

2. The compound of claim 1 wherein Y is a normal, branched or cyclic $C_6$–$C_{24}$-alkyl group.

3. The compound of claim 1 wherein $R_2$–$R_9$ are each, independently, a hydrogen atom or a linear, branched or cyclic $C_1$–$C_6$-alkyl group.

4. A compound of Formula I,

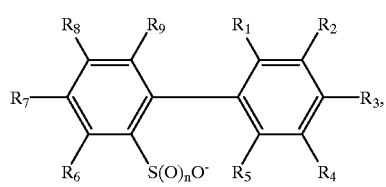

(I)

wherein $R_2$–$R_9$ are each, independently, hydrogen, a substituted or unsubstituted, normal, branched or cyclic alkyl group, a substituted or unsubstituted aryl group, an hydroxyl group, an amino group, an alkoxy group, a cyano group, a nitro group or a halogen atom; n is 1 or 2; and $R_1$ is a moiety of the formula $HOCH_2CH_2(OCH_2CH_2)_mO$— or $CH_3CH(OH)CH_2(OCH(CH_3)CH_2)_mO$—, wherein m is an integer from 0 to about 20.

5. A compound of Formula II,

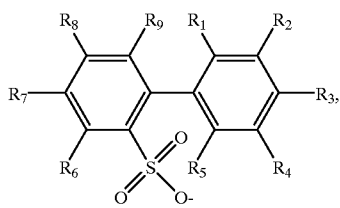

(II)

wherein $R_2$–$R_9$ are each, independently, a hydrogen atom or a straight chain or branched $C_1$–$C_{24}$-alkyl group; at least one of $R_2$–$R_5$ is a sulfonate group and the remainder are each, independently, a hydrogen atom or a normal, branched or cyclic $C_1$–$C_{24}$-alkyl group; $R_1$ is a hydroxyl group, a group YC(O)O— or YO—, wherein Y is a hydrogen atom or a hydrophobic group; or a moiety of the formula $HOCH_2CH_2(OCH_2CH_2)_mO$— or $CH_3CH_2CH_2O(CH(CH_3)CH_2O)_m$—, wherein m is an integer from 0 to about 20.

6. A method of producing a compound of Formula I,

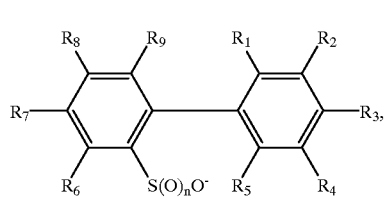

(I)

wherein $R_2$–$R_9$ are each, independently, hydrogen, a substituted or unsubstituted, normal or branched alkyl group, a substituted or unsubstituted aryl group, an hydroxyl group, an amino group, an alkoxy group, a cyano group, a nitro group or a halogen atom; $R_1$ is a group of the formula YC(O)O— wherein Y is a normal, branched or cyclic, substituted or unsubstituted alkyl group; and n is 1 or 2; comprising the step of reacting a compound of Formula III,

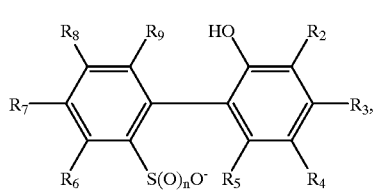

(III)

wherein $R_2$–$R_9$ and n have the meanings given above, with a carboxylic acid or activated carboxylic acid of the formula Y—C(=O)X, wherein Y has the meaning given above and X is —OH or a leaving group.

7. The method of claim 6 wherein Y is a normal, branched or cyclic, substituted or unsubstituted $C_3$–$C_{24}$-alkyl group.

8. The method of claim 6 wherein X is a leaving group selected from the group consisting of chloride, p-toluenesulfonate, 1-imidazolyl, and carboxylate.

9. A method of producing a compound of Formula I,

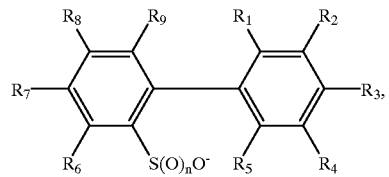

(I)

wherein $R_2$–$R_9$ are each, independently, hydrogen, a substituted or unsubstituted, normal or branched alkyl group, a substituted or unsubstituted aryl group, an hydroxyl group, an amino group, an alkoxy group, a cyano group, a nitro group or a halogen atom; $R_1$ is a group of the formula YO—, wherein Y is a normal, branched or cyclic, substituted or unsubstituted alkyl group; and n is 1 or 2; comprising the step of reacting a compound of Formula III,

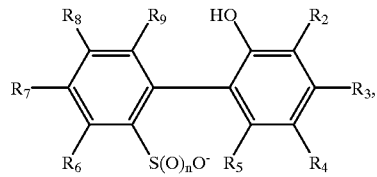

(III)

wherein $R_2$–$R_9$ and n have the meanings given above, with a compound of the formula YX, wherein Y has the meaning given above and X is a leaving group.

10. The method of claim 9 wherein Y is a normal, branched or cyclic, substituted or unsubstituted $C_3$–$C_{24}$-alkyl group.

11. The method of claim 10 wherein X is selected from the group consisting of chloride, bromide, iodide, methanesulfonate and p-toluenesulfonate.

* * * * *